United States Patent [19]

van Schoonhoven

[11] Patent Number: 5,037,306
[45] Date of Patent: Aug. 6, 1991

[54] TRAINING DEVICE FOR AN AUTOMATIC INJECTOR

[75] Inventor: Hendrik A. van Schoonhoven, Olst, Netherlands

[73] Assignee: Duphar International Research B.V., Weesp, Netherlands

[21] Appl. No.: 597,352

[22] Filed: Oct. 10, 1990

[30] Foreign Application Priority Data

Oct. 24, 1989 [NL] Netherlands ............... 8902630

[51] Int. Cl.⁵ .................. G09B 23/28; A61M 5/20
[52] U.S. Cl. ............................. 434/262; 604/134; 604/135
[58] Field of Search ............... 604/134, 135, 136, 68; 173/121; 434/262; 72/433, 434; 401/81, 180, 54

[56] References Cited

U.S. PATENT DOCUMENTS 3,797,489  3/1974  Sarnoff ..................... 604/136
4,820,286  4/1989  van der Wal ............... 604/134

Primary Examiner—Richard J. Apley
Assistant Examiner—Karen G. Horowitz
Attorney, Agent, or Firm—Stevens, Davis, Miller & Mosher

[57] ABSTRACT

The invention relates to a training device for an automatic injector, comprising a cylindrical outer sleeve, in the rear portion of which a discharge mechanism is connected and in the front portion of which a holder for a punch member is accommodated so as to be locked against forward movement. The discharge mechanism comprises a plunger, a coil spring which acts on the plunger, a locking device and a safety member. The holder for the punch member comprises a sleeve-like rear portion which is open at each end. The punch member is accommodated in the holder so that the front prod-shaped end portion, which has such dimensions that it can pass throuogh the central aperture in the nose portion of the holder outward, is present inside the holder prior to use of the device. The rear end portion of the punch member comprises means which, in cooperation with means provided on the inner wall of the resilient sleeve-like rear portion of the holder, prevent undesired backward movement of the punch member in the holder in which, however, at the area of said means the device is proportioned so that after activation the wall of the holder can expand resiliently outward within the outer sleeve so as to allow the punch member to pass. A spring is present between the punch member and the locking device which enables locking of the plunger, making the device ready for reuse.

4 Claims, 1 Drawing Sheet

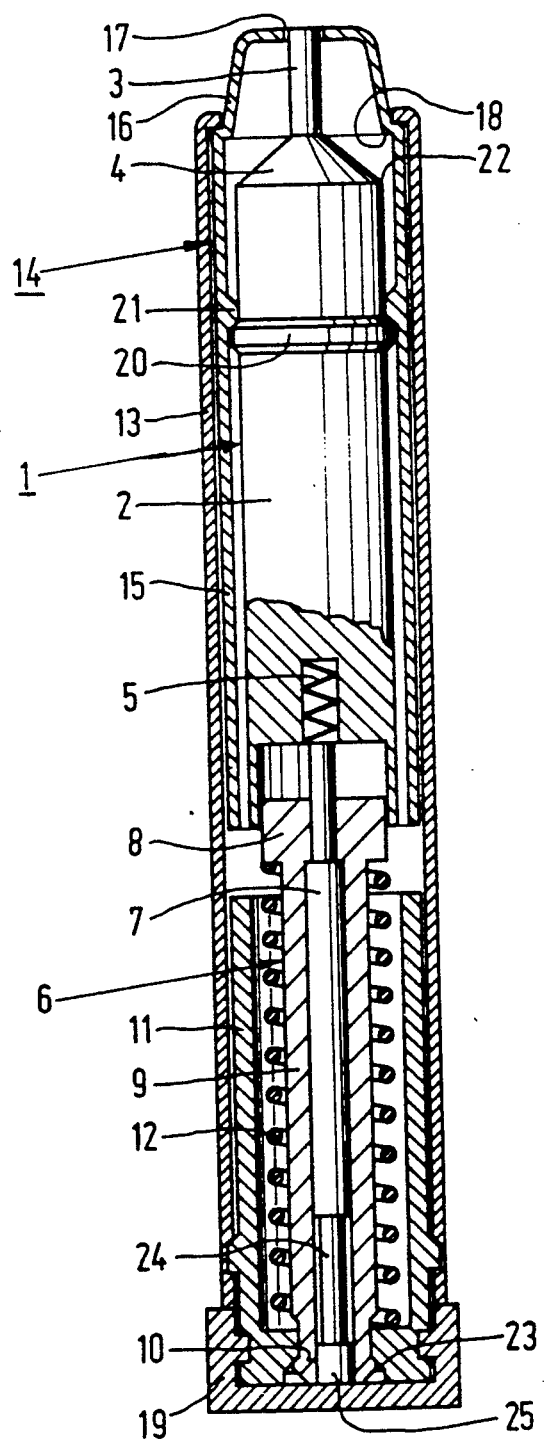

TRAINING DEVICE FOR AN AUTOMATIC INJECTOR

The invention relates to a training device for an automatic injector, comprising a cylindrical outer sleeve into the rear portion of which a discharge mechanism is connected and into the front portion of which a holder intended for accommodating a punch member is incorporated so as to be locked against forward movement.

The discharge mechanism comprises a pistol sleeve which is open at its front end, a plunger which is movable in said pistol sleeve a coil spring which acts on the plunger and tries to move same out of the front end of the pistol sleeve outwards a locking device which cooperates with said plunger so as to prevent undesired forward movement thereof, and a safety member to block unintentional unlocking of the locking device.

After removal of the safety member, the locking of the plunger is removed by a backward movement of the holder with the punch member with respect to the outer sleeve, and the device is activated.

The holder for the punch member comprises a sleeve like rear portion which is open at each end and which, after activating the device, is traversed by a rear end portion of the punch member, and a nose portion which comprises a central aperture and which serves to stop the forward movement of the punch member in the holder after activating the device and to allow the front end portion of said member to pass.

The punch member is accommodated in the holder so that its front prod-shaped end portion, which has such dimension that it can pass through the central aperture in the nose portion of the holder outwards, is present within the holder prior to use of the device.

Such a training device is known from U.S. Pat. No. 3,795,061, with the proviso that the pistol sleeve for the discharge mechanism forms one assembly with the holder and the nose portion of the holder constitutes a separate component ("end cap").

Automatic injectors are designed in particular for use by persons who, at a given instant which is not known before-hand, have to administer an injection into their own body. Such persons include, for example, soldiers after having been exposed to an enemy's battle gas, for example, a nerve gas. It will therefore be obvious that the user may not hesitate to inject himself at the critical moment when the injection is required. As a matter of fact, the user's life will at that instant depend on the accurate manipulation of the injector. The rapid and accurate use of an automatic injector is also a first requirement in the so called "buddy help", giving help to a wounded and/or panicked buddy in the battle field. An automatic injector intended especially for this purpose has also been developed. The fear of administering to oneself or a buddy an injection at a critical moment must hence be overcome previously by training.

The following requirements have to be imposed upon such a training device:

(1) the training device must simulate the action of the automatic injector as well as possible, of course without the injection being administered, and (2) it must be possible to use the training device over and over again and to make it ready for reuse very easily.

It is exactly with respect to the second requirement that the training device described in the above U.S. Pat. No. 3,795,061 is unsatisfactory. This known training device comprises a return spring which, after activating the device, serves to partly compensate for the driving force of the driving spring before the forward movement of the punch member is stopped by the end cap However, in order to satisfy the first requirement, the force with which the front prod-shaped end portion of the punch-member emanates outwards from the nose of the device must be very considerable. As a matter of fact, the device in use must simulate as readily as possible the automatic injector which must comprise a powerful driving spring to overcome the resistance when injecting through the battle dress. In order to in addition overcome the resistance of the return spring, a very powerful driving spring must hence be used. As a result of this, the training device will be subject to greater detrition during use, so that the reuse is restricted. It has been found that a training device as described in the U.S. Pat. No. 3,795,061 can at best be used only ten times, whereas the military authorities impose the requirement that such a device must be useable at least approximately fifty times In preparing the device for reuse the spring force of the driving spring must be overcome; the oppositely directed spring force of the return spring contributes to this "recocking" of the driving spring. However, during said recocking, not only does the spring force of the driving spring increases, but the compensating force exerted by the return spring decreases. As a result of this the recocking of the driving spring, in particular the last phase hereof, is impeded. So the construction with two coil springs as is known from the United States Patent discussed above is an impediment in making the device ready for reuse. An extra disadvantage of the device known from said United States Patent is the separately supplied tool which is necessary to make the device ready for reuse.

In order to meet the above-mentioned disadvantages, in U.S. Pat. No. 4,640,686 it is proposed to use a training device for an automatic injector which produces an audible signal However, the disadvantage of such a device is that in use an automatic injector is insufficiently simulated. The forces occurring during the use of an automatic injector give the user a certain emotional sensation which is quite different from an audible signal.

It is the object of the present invention to provide a training device for an automatic injector which can be used considerably more frequently that the device known from U.S. Pat. No. 3,795,061 and which can be made ready for reuse much more easily.

This object can be achieved by means of a training device as described in the opening paragraph which is characterised according to the present invention in that the rear end portion of the punch member comprises means which, in cooperation with means provided on the inner wall of the resilient sleeve-like rear portion of the holder. prevent undesired forward movement of the punch member in the holder, in which, however, the device at the area of said means is proportioned so that after activation the wall of the holder can expand resiliently outwards within the outer sleeve so as to allow the punch member to pass, and spring means are present between the punch member and the locking device which enable locking of the plunger when the device is made ready for reuse.

It has been found that the use of the above-mentioned means to stop the punch member in the holder makes the use of a return spring superfluous. As a result of this a less powerful driving spring will suffice to nevertheless obtain an optimum simulation, i.e. to give the user a sensation which resembles as well as possible the sensation he gets from an injection with an automatic injector. Omitting the return spring facilitates the recocking of the driving spring and hence the preparing of the device for reuse. Furthermore it has been found surprisingly that the number of times the training device may be reused has been increased considerably by omitting the return spring and by using the above-described measures. It has been found that the training device according to the invention can readily be used fifty times. An extra advantage of the device according to the invention over the known device is the reduction in cost-price by omitting one component, namely the return spring; in addition, this simplifies the assembly. In the construction of the device according to the invention the plunger may be manufactured from a synthetic material. This is favorable as compared with the same component ("collet") from U.S. Pat. 3,795,061 which, in connection with the forces acting on it, has to be manufactured from metal It is a further particular advantage that a separate tool ("recocking tool") is not necessary to make the device according to the invention ready for reuse; simple spring means in the device itself have proven to be sufficient for this purpose.

In a favorable embodiment the device according to the invention is constructed so that the rear end portion of the punch member comprises a circumferential externally projecting ridge or an annular member the front face of which engages a number of radially arranged, inwardly projecting raised portions which are provided on the inner wall of the sleeve-like rear portion of the holder, said portion having a five-to fourteen sided cross-section, the ridge or the annular member on the punch member and the raised portions on the inner wall of the holder being mutually proportioned so that after activating the device the raised portions are pushed aside ("overridden") by the ridges or by the annular member so that the forward movement of the punch member in the holder is then not impeded. A holder is preferably used which comprises raised portions on the inner wall, as described in European Patent Specification 0,186,916. The holder known from this Patent Specification is intended for an automatic injector and has for its object to improve the shock resistance of the injector, namely to prevent that, when the injector is dropped, the cartridge in the holder moves forward so that the tip of the needle can emanate.

In a further preferred embodiment the locking device for the discharge mechanism of the device according to the invention comprises a pin which extends through a central aperture in the plunger till beyond the front and hereof and which is coaxial with the spring means mentioned hereinbefore, said spring means being mounted in a central recess in the rear end portion of the punch member. The spring means may be a coil spring which acts in the direction of the plunger. The rear end portion of the locking pin, in cooperation with the plunger, keeps the punch member locked prior to use of the device. After removing the safety member, said locking can be removed by a backward movement of the holder with the punch member with respect to the outer sleeve, said movement being transferred to the pin by said spring means and resulting in a backward movement of the pin in the central aperture of the plunger.

The locking between the plunger and locking pin is preferably constructed so that the plunger comprises at its rear end at least two resilient prongs which engage with conical surfaces behind a corresponding conical end face around a central aperture in the rear wall of the pistol sleeve, the locking pin with its rear end portion tightly fits within the resilient prongs and in this manner keeps the plunger locked in the pistol sleeve prior to use of the device, and the rear end portion of the locking pin is preceded by a portion having a reduced diameter (reduced portion), as a result of which in the case of a backward movement of the locking pin in the central aperture of the plunger the plunger prongs can move inwardly at the area of the reduction and can disengage from the engagement with the pistol sleeve.

The last-mentioned preferred construction provides reliable locking but is also reliable during use of the device. As a matter of fact, a backward movement of the holder with the punch member with respect to the outer sleeve causes a backward movement of the locking pin with respect to the plunger. When the pin has moved backwards to such an extent that the resilient prongs at the area of the reduction can resiliently move inwardly, the prongs disengage from the engagement with the pistol sleeve connected in the outer sleeve and the plunger is moved forward under the influence of the coil spring 12 (driving spring). This movement is transmitted to the punch member The invention will now be described in greater detail with reference to a preferred embodiment which is presented in the drawing which shows a training device according to the invention, partly as a longitudinal sectional view, partly broken away and as a side elevation.

The training device shown comprises a punch member 1, shown partly as a longitudinal sectional view and partly as a side elevation, the rear end portion 2 of which has a substantially uniform diameter throughout its length and the prod-shaped front end portion 3 of which is connected to the rear end portion via a conical intermediate portion 4. A central recess is provided in the rear end portion of the punch member in which recess a coil spring 5 is accommodated which can be used as a recocking spring. This recocking spring is in a coaxial position with respect to locking pin 7 accommodated in a central aperture of plunger 6. The synthetic material plunger comprises at its front end a plunger head 8 at some distance from the rear end of the punch member and a tubular central portion 9 which at its rear end terminates in two resilient prongs 10. The plunger, together with a pistol sleeve 11, keeps a coil spring 12 enclosed as a power source. The pistol sleeve is locked in an outer sleeve 13 which also keeps a holder 14 for the punch member locked against forward movement. The holder consists of a sleeve-like rear portion 15 having a heptagonal cross-section and a nose portion 16 which comprises a central aperture 17. This aperture is proportioned so that, after activating the device the prod-shaped front end portion 3 of the punch member can pass outwards through the aperture. The rear end 18 of the nose portion forms an abutment for the shoulder 22 formed by the conical intermediate portion 4 of the punch member. The "stroke" is determined by the distance between said shoulder and the abutment therefor in the nose portion of the holder. The device further comprises a safety member in the form of a cap 19. Locking and safety will be described in greater detail hereinafter. The punch member comprises a circumferential outwardly projecting ridge 20 the front face of which engages a number of raised portions 21 radially situated on the inner wall of the resilient sleeve-loke portion 15 of the holder. The circumferential ridge on the punch member, in cooperation with the raised portions 21, prevents any undesired forward movement of the punch member in the holder. After activating the device the punch member is moved forward by the releasing spring 12, the ridge easily passing the raised portions on the inner wall of the holder; the resilient wall of the sleeve like portion of the holder expands at the area of the raised portions. The forward movement of the punch member in the holder is stopped when the shoulder 22 contacts the abutment 18 formed by the nose 16 of the holder. The prod-shaped front end portion 3 of the punch member has then emanated over a length equal to the "stroke". After using the device, it may be made ready for reuse, recocking spring 5 being used. In this manner the device can easily be locked and be made ready for reuse. Locking, safety and recocking, i e making the device ready for reuse, will be described with reference to the device shown For using the device, first the safety cap 19 is removed. The safety cap should be firmly connected to the pistol sleeve, which means that it should not allow any axial movement with respect to the pistol sleeve; a suitable detachable connection therefor is a snap connection or a bayonet catch. The device is now provided on a suitable part of the body, for example the upper leg, and is pressed. The holder 14 in the outer sleeve 13 is moved backwards, which results in a relative backward movement of punch member 1 and locking pin 7 with respect to the plunger 6. The rear end of the plunger comprises two resilient prongs 10 which extend through a central aperture in the rear wall of the pistol sleeve and engage with their conical faces behind a corresponding conical end face 23 around the said aperture. Because the safety cap 19 has been removed, the locking pin 7 can move rearwards until its reduced portion 24 has reached the resilient prongs 10. The prongs can now move towards each other as a result of the conical tapering of the engaging surfaces between prongs and pistol sleeve and as a result of the forwardly directed force of the coil spring 12 on said plunger. As a result of this the prongs and hence the plunger, are unlocked after which plunger and punch member shoot forward under the influence of the coil spring. In the extreme outward position of the prod-shaped front portion 3, the punch member is stopped by the abutment 18 in the nose portion of the holder. In contrast with the device known from U.S. Pat. No. 3,795,061, the force in unlocking the above-described device is not directed perpendicularly to the shearing face of the plunger (in fact: conical engaging surfaces), as a result of which the reproducibility of the discharge force is promoted. Upon recocking, the prod-shaped end portion of the punch member is pushed inwardly, the holder also moving slightly backwards in the outer sleeve. The resilient prongs of the plunger are forced through the central aperture in the rear wall of the pistol sleeve. By pushing the locking pin 7 during said operation against the action of the recocking spring 5 inwardly, for example, by means of the thumb, the resilient prongs of the plunger can be locked behind the rear wall of the pistol sleeve by means of the end portion 25 of the locking pin. The conical surfaces of the prongs 10 then bear on the conical end face 23 around the central aperture in the rear wall of the pistol sleeve 11. The device is now ready again for use.

I claim:

1. A training device for an automatic injector comprising a punch member and cylindrical outer sleeve comprising in its rear portion a discharge mechanism and in its front portion a holder for the punch member so as to lock the punch member against forward movement, wherein the discharge mechanism comprises a pistol sleeve which is open at its front end, a plunger which is movable in the pistol sleeve, a coil spring which acts on the plunger to move the plunger out of the front end of the pistol sleeve outward, a locking device slidably positioned in a portion of the plunger which cooperates with the plunger to prevent undesired forward movement thereof, and a safety member to block unintentional unlocking of the locking device;

wherein said locking device comprises a pin including means which allow the pin to remain at least for the greater part within the plunger when the plunger is unlocked;

such that, after removing the safety member, the plunger is unlocked by a backward movement of the holder and punch member with respect to the outer sleeve, activating the device;

wherein the holder for the punch member comprises a sleeve-like rear portion which is open at each end and which, after activating the device, is traversed by a rear end portion of the punch member, and a nose portion, said nose portion of the holder comprising a central aperture and serving to stop the forward movement of the punch member in the holder after the device is activated, and allowing a front end portion of the punch member to pass;

in which the punch member is accommodated in the holder such that its front prod-shaped end portion, which is dimensioned such that it can pass through the central aperture in the nose portion of the holder outward, is inside the holder prior to use;

such that the rear end portion of the punch member comprises means which, in cooperation with means provided on an inner wall of the resilient sleeve-like rear portion of the holder, prevents undesired forward movement of the punch member in the holder, in which the device is proportioned such that after being activated, the wall of the holder can expand resiliently outward with the outer sleeve to allow the punch member to pass; and wherein the device further comprise spring means interposed between the punch member and the locking device which enables locking of the plunger when the device is ready for reuse.

2. A device as claimed in claim 1, characterised in that the rear end portion of the punch member comprises a circumferential outwardly projecting ridge or an annular member the front face of which engages a number of radially arranged inwardly projecting raised portions provided on the inner wall of the sleeve-like rear portion of the holder, which portion has a five-to fourteen-sided cross-section, the ridge or the annular member on the punch member and the raised portions on the inner wall of the holder being mutually proportioned so that after activating the device the raised portions are pushed aside by the ridges or by the annular member so that the forward movement of the punch member in the holder is then no impeded.

3. A device as claimed in claim 1 or 2, characterised in that the locking device for the discharge mechanism comprises a pin which extends through a central aperture in the plunger till beyond the front end thereof and which is coaxial with said spring means, said spring means being accommodated in a central recess in the rear end portion of the punch member, wherein the rear end portion of the locking pin, in cooperation with the plunger, keeps the discharge mechanism locked prior to use of the device, but in which, after removing the safety member, said locking can be removed by a backward movement of the holder with the punch member with respect to the outer sleeve, which movement is transferred to the pin by said spring means and results in a backward movement of the pin in the central aperture of the plunger.

4. A device as claimed in claim 3, characterized in that the plunger at its rear end comprises at least two resilient prongs which engage with conical surfaces behind a corresponding conical end face around a central aperture in the rear wall of the pistol sleeve, the rear end portion of the locking pin tightly fits within the resilient prongs and in this manner keeps the plunger locked in the pistol sleeve prior to use of the device, and the rear end portion of the locking pin is preceded by a portion of reduced diameter (reduced portion), as a result of which during the backward movement of the locking pin in the central aperture of the plunger the plunger prongs can move resiliently inwardly at the area of the reduced portion and can disengage from the engagement with the pistol sleeve while the pin remains at least for the greater part in said central aperture in the plunger.

* * * * *